(12) United States Patent
Goldberger

(10) Patent No.: US 8,603,086 B2
(45) Date of Patent: Dec. 10, 2013

(54) METHOD FOR PREVENTING THROMBUS FORMATION

(75) Inventor: Jeffrey J. Goldberger, Skokie, IL (US)

(73) Assignee: Gold-T Tech, Inc., Skokie, IL (US)

( * ) Notice: Subject to any disclaimer, the term of this patent is extended or adjusted under 35 U.S.C. 154(b) by 0 days.

(21) Appl. No.: 11/118,742

(22) Filed: Apr. 29, 2005

(65) Prior Publication Data

US 2005/0222622 A1 Oct. 6, 2005

Related U.S. Application Data

(63) Continuation of application No. 10/364,143, filed on Feb. 10, 2003, now abandoned.

(60) Provisional application No. 60/356,200, filed on Feb. 11, 2002.

(51) Int. Cl.
*A61M 31/00* (2006.01)

(52) U.S. Cl.
USPC .......... 606/41; 601/2; 601/3; 606/45; 606/47; 606/49; 607/96; 607/98; 607/99; 607/100; 607/101

(58) Field of Classification Search
USPC .............. 606/41, 45, 47, 49; 607/96, 98–101; 601/2, 3
See application file for complete search history.

(56) References Cited

U.S. PATENT DOCUMENTS

| 4,277,227 A | 7/1981 | Jenkins |
|---|---|---|
| 4,281,669 A | 8/1981 | MacGregor |
| 4,403,988 A | 9/1983 | Binard et al. |
| 4,494,531 A | 1/1985 | Gianturco |
| 4,710,172 A | 12/1987 | Jacklich et al. |
| 4,725,275 A | 2/1988 | Moll |
| 4,801,452 A | 1/1989 | Hunter et al. |
| 4,832,055 A | 5/1989 | Palestrant |
| 4,873,083 A | 10/1989 | Hunter et al. |
| 4,935,030 A | 6/1990 | Alonso |
| 5,326,372 A | 7/1994 | Mhatre et al. |

(Continued)

FOREIGN PATENT DOCUMENTS

| CA | 2367631 | 7/2002 |
|---|---|---|
| CN | 2115768 | 9/1992 |
| DE | 3209721 | 9/1983 |
| JP | 04017862 | 1/1992 |

OTHER PUBLICATIONS

International Search Report for International Application No. PCT/US03/03884, issued on Nov. 25, 2003.

(Continued)

*Primary Examiner* — Aaron Roane
(74) *Attorney, Agent, or Firm* — Fitch, Even, Tabin & Flannery LLP

(57) ABSTRACT

The present invention provides devices and methods for preventing or significantly reducing the risk of thrombus formation. More specifically, the devices and methods of the present invention provide energy to blood flowing within a chamber or vessel to prevent or reduce blood stasis and thereby prevent or significantly reduce the risk of thrombus formation. The present invention is ideally suited for prevention or reduction of risk of blood clot formation in the atria in patients with atrial fibrillation, in blood vessels of patients at risk of clot formation, in areas adjacent to, or on, artificial heart valves or other artificial cardiovascular devices, and the like.

7 Claims, 5 Drawing Sheets

(56) References Cited

U.S. PATENT DOCUMENTS

| | | | |
|---|---|---|---|
| 5,354,330 A | 10/1994 | Hanson et al. | |
| 5,399,158 A * | 3/1995 | Lauer et al. | 604/22 |
| 5,430,023 A | 7/1995 | Gesellchen et al. | |
| 5,445,608 A | 8/1995 | Chen et al. | |
| 5,487,760 A * | 1/1996 | Villafana | 623/2.2 |
| 5,509,896 A | 4/1996 | Carter | |
| 5,549,119 A | 8/1996 | Solar | |
| 5,620,409 A | 4/1997 | Venuto et al. | |
| 5,624,380 A | 4/1997 | Takayama et al. | |
| 5,695,460 A | 12/1997 | Siegel et al. | |
| 5,700,634 A | 12/1997 | Speck | |
| 5,725,494 A | 3/1998 | Brisken | |
| 5,725,550 A | 3/1998 | Nadal | |
| 5,728,062 A | 3/1998 | Brisken | |
| 5,735,811 A | 4/1998 | Brisken | |
| 5,846,218 A | 12/1998 | Brisken et al. | |
| 5,858,972 A | 1/1999 | Pierschbacher et al. | |
| 5,864,017 A | 1/1999 | Brubaker | |
| 5,876,971 A | 3/1999 | Noeske-Jungblut et al. | |
| 5,931,805 A | 8/1999 | Brisken | |
| 5,944,751 A | 8/1999 | Laub | |
| 5,951,981 A | 9/1999 | Markland, Jr. et al. | |
| 5,952,296 A | 9/1999 | Bigazzi | |
| 5,964,694 A | 10/1999 | Siess et al. | |
| 5,967,986 A | 10/1999 | Cimochowski et al. | |
| 5,967,989 A | 10/1999 | Cimochowski et al. | |
| 5,972,019 A | 10/1999 | Engelson et al. | |
| 6,007,558 A | 12/1999 | Ravenscroft et al. | |
| 6,008,019 A | 12/1999 | Baldus et al. | |
| 6,013,093 A | 1/2000 | Nott et al. | |
| 6,015,387 A | 1/2000 | Schwartz et al. | |
| 6,022,309 A | 2/2000 | Celliers et al. | |
| 6,024,718 A | 2/2000 | Chen et al. | |
| 6,030,334 A | 2/2000 | Cox et al. | |
| 6,034,094 A | 3/2000 | Losel et al. | |
| 6,066,149 A | 5/2000 | Samson et al. | |
| 6,068,645 A | 5/2000 | Tu | |
| 6,086,573 A | 7/2000 | Siegel et al. | |
| 6,113,570 A * | 9/2000 | Siegel et al. | 604/507 |
| 6,133,422 A | 10/2000 | Rosen et al. | |
| 6,156,007 A * | 12/2000 | Ash | 604/113 |
| 6,156,540 A | 12/2000 | Rosen et al. | |
| 6,210,393 B1 | 4/2001 | Brisken | |
| 6,210,404 B1 | 4/2001 | Shadduck | |
| 6,214,025 B1 | 4/2001 | Thistle et al. | |
| 6,221,038 B1 | 4/2001 | Brisken | |
| 6,228,046 B1 | 5/2001 | Brisken | |
| 6,233,479 B1 | 5/2001 | Haddad et al. | |
| 6,235,707 B1 | 5/2001 | Bajusz et al. | |
| 6,239,101 B1 | 5/2001 | Esmon et al. | |
| 6,261,820 B1 | 7/2001 | Boone et al. | |
| 6,287,272 B1 | 9/2001 | Brisken et al. | |
| 6,296,619 B1 | 10/2001 | Brisken et al. | |
| 6,361,554 B1 | 3/2002 | Brisken | |
| 6,372,498 B2 | 4/2002 | Newman et al. | |
| 6,387,116 B1 | 5/2002 | McKenzie et al. | |
| 6,398,734 B1 | 6/2002 | Cimochowski et al. | |
| 6,400,982 B2 | 6/2002 | Sweeney et al. | |
| 6,421,565 B1 | 7/2002 | Hemmingsson | |
| 6,432,068 B1 | 8/2002 | Cori et al. | |
| 6,464,660 B2 | 10/2002 | Brisken et al. | |
| 6,464,680 B1 | 10/2002 | Brisken et al. | |
| 6,494,874 B1 | 12/2002 | Brisken | |
| 6,503,243 B1 | 1/2003 | Brisken | |
| 6,508,775 B2 | 1/2003 | McKenzie et al. | |
| 6,654,638 B1 * | 11/2003 | Sweeney | 607/9 |
| 6,985,774 B2 * | 1/2006 | Kieval et al. | 607/44 |
| 7,039,453 B2 * | 5/2006 | Mullick et al. | 600/476 |
| 2004/0015104 A1 | 1/2004 | Goldberger | |

OTHER PUBLICATIONS

United States Patent and Trademark Office, Non-Final Office Action in related U.S. Appl. No. 10/364,143, dated Nov. 1, 2004, 10 pages.

Search results dated Dec. 13, 2001, 17 pages.

Zauhar et al., Studies of Acoustic Streaming in Biological Fluids with an Ultrasound Dopple Technique, The British Journal of Radiology 71 (1998), 297-302, 6 pages.

Shi et al., Quantitative Investigation of Acoustic Streaming in Blood, J. Acoust. Soc. Am. 111 (2), Feb. 2002, 12 pages.

"Baroreceptor," http://en.wikipedia.orgiwiki/baroreceptor, Wikipedia, accessed Sep. 7, 2006, 2 pages.

Davos et al., The Effect of Baroreceptor Activity on Cardiovascular Regulation, Hellenic Journal of Cardiology 43: 145-155, 2002, 11 pages.

Weyman, "Left Ventricular Inflow Tract II: The Left Atrium, Pulmonary Veins, and Coronary Sinus," In: Bussy R (ed.), Principles and Practice of Echocardiography, Philadelphia: Lea & Febiger, p. 471-497, (1994) 27 pages.

* cited by examiner

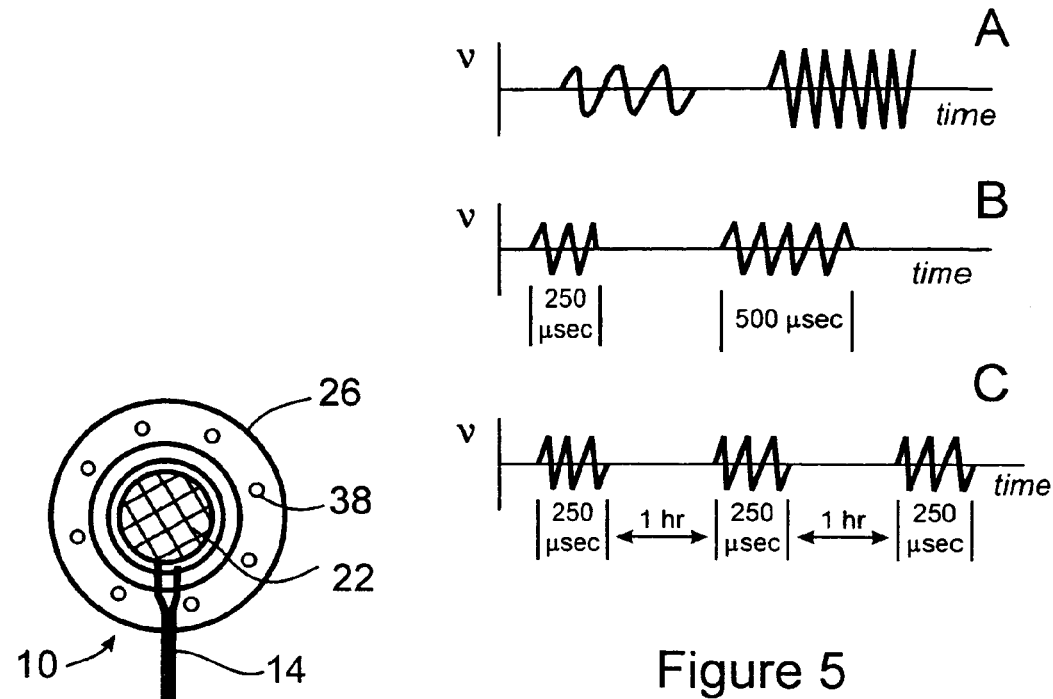
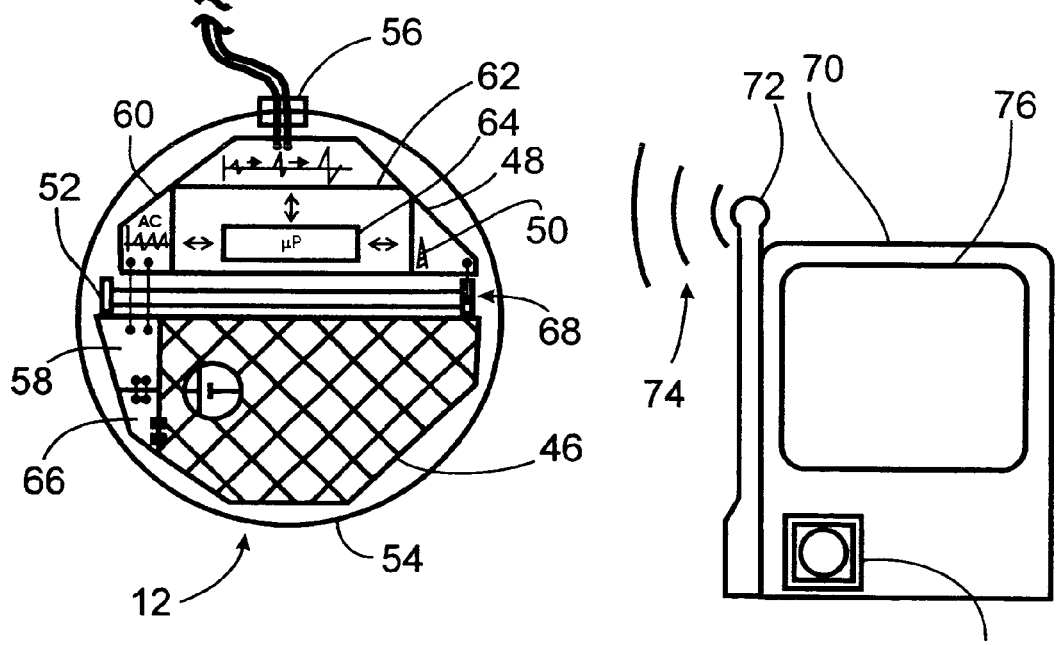
Figure 4
Figure 5

METHOD FOR PREVENTING THROMBUS FORMATION

RELATED APPLICATION

This application is a continuation of prior application Ser. No. 10/364,143, filed on Feb. 10, 2003, now abandoned, which was based on, and claimed benefit, of U.S. Provisional Application Ser. No. 60/356,200, filed on Feb. 11, 2002, all of which are hereby incorporated by reference.

FIELD OF THE INVENTION

The present invention is related to devices and methods for preventing or significantly reducing the risk of thrombus formation. More specifically, the devices and methods of the present invention provide energy to blood flowing within a chamber or vessel to prevent or reduce blood stasis and thereby prevent or significantly reduce the risk of thrombus formation. Additionally, the devices and methods of the present invention provide energy to the surface of the chamber or vessel, thereby preventing or reducing thrombus growth at the blood/surface interface. The present invention is ideally suited for prevention or reduction of risk of blood clot formation in the atria in patients with atrial fibrillation, in blood vessels of patients at risk of clot formation, in areas adjacent to, or on, artificial heart valves or other artificial cardiovascular devices, and the like.

BACKGROUND

Stroke occurs in approximately 600,000 people in the United States yearly and is associated with significant morbidity and mortality. In 1998, 158,448 people died as a result of stroke. Over 45 billion dollars of health care costs are attributable to stroke in a year. Approximately 4.5 million stroke survivors are alive today. 2001 Heart and Stroke Statistical Update, American Heart Association.

There are a number of important causes of stroke. These include thrombotic, embolic, and hemorrhagic causes. Embolic strokes account for approximately one quarter of all strokes. In embolic strokes, a blood clot or other material travels to the brain from another site and occludes a blood vessel, thereby depriving the brain of the needed blood flow (and associated oxygen and glucose supplies); this results in the death of the cells that are usually supplied by this blood flow. The most common source for these emboli is the heart. Blood clots, otherwise known as thrombi, can form in patients with atrial fibrillation, heart valves, artificial materials (e.g., artificial hearts, vascular stents, and the like), or significant heart disease. It is estimated that 15 percent of all strokes occur in patients with atrial fibrillation. 2001 Heart and Stroke Statistical Update, American Heart Association.

The normal electrical rhythm of the top chambers of the heart (i.e., the atria) is sinus rhythm. Normal sinus rhythm is typically characterized by a rate of about 60 to about 100 beats/minute under normal circumstances. With exercise, the heart rate may increase up to about 180 beats/minute. In normal sinus rhythm, the electrical activation of the atrium results in contraction of this chamber and emptying of blood into the ventricles (the lower chambers of the heart). Atrial flutter or fibrillation are abnormally rapid and/or chaotic rhythms that are characterized by rates of about 300 to 400, or more, beats/minute in the atrium. Instead of a single wavefront of electrical activation with sinus rhythm, atrial fibrillation presents multiple, simultaneous wavefronts. Because of the rapid rate and the multiple electrical wavefronts, there is no significant coordinated atrial contraction. Because of the lack of atrial contraction in patients with atrial fibrillation, the blood flow through the atrium may be sluggish, allowing for the formation of blood clots. If these blood clots leave the atrium and travel to the brain, they may cause an embolic stroke. Because of the high risk for thromboembolism (i.e., formation of blood clots and their travel through the vascular system) in many patients with atrial fibrillation, these patients are typically treated with a blood thinner (e.g., coumadin) to help prevent blood clot formation. The use of blood thinners such as coumadin can reduce the risk of stroke by up to about 75 percent. Unfortunately, some patients cannot take coumadin due to the risk of bleeding; they may, for example, be at a high risk for complications or have bleeding problems. It is estimated that up to about 5 percent of patients develop major bleeding as a result of coumadin therapy.

There are other medical conditions also associated with thrombus formation that are currently treated with coumadin. Patients with artificial valves or other implanted artificial materials are frequently treated with coumadin to prevent thrombus formation. Blood clot formation on an artificial valve or other implanted surface can cause stroke and/or can prevent the artificial valve or other implant from functioning properly. Patients may also be at risk for forming blood clots in their blood vessels or chambers due to poor flow characteristics. These conditions are treated with coumadin.

Currently, there are no effective alternatives to the use of coumadin or other blood thinners for the treatment of these patients. It would be desirable, therefore, to provide alternative methods for preventing or significantly reducing the risk of thrombus formation. It would also be desirable to provide methods for preventing or significantly reducing the risk of thrombus formation which could be used separately or in combination with blood thinners to provide treatment options for essentially all patients at risk for thrombus formation. The present invention provides such methods as well as devices for carrying out such treatment methods.

SUMMARY OF THE INVENTION

The present invention is related to devices and methods for preventing or significantly reducing the risk of thrombus formation. More specifically, the devices and methods of the present invention provide energy to blood flowing within a chamber or vessel to prevent or reduce blood stasis and thereby prevent or significantly reduce the risk of thrombus formation. Additionally, the devices and methods of the present invention provide energy to the surface of the chamber or vessel, thereby preventing or reducing thrombus growth at the blood/surface interface. The present invention is ideally suited for prevention or reduction of risk of blood clot formation in the atria in patients with atrial fibrillation, in blood vessels of patients at risk of clot formation, in areas adjacent to, or on, artificial heart valves or other artificial cardiovascular devices, and the like.

More specifically, the present invention provides a method for preventing thrombus formation or reducing the risk of thrombus formation in a patient at risk for thrombus formation, said method comprising providing the patient with a source of energy adjacent to or within a vessel or chamber containing flowing blood and activating the source of energy to provide energy to the flowing blood within the vessel or chamber whereby blood movement within the vessel or chamber is increased, thereby preventing thrombus formation or reducing the risk of thrombus formation. Additionally, the devices and methods of the present invention provide energy to the surface of the chamber or vessel, thereby preventing or reducing thrombus growth at the blood/surface interface.

Additionally, the present invention provides an implantable device for preventing thrombus formation or reducing the risk of thrombus formation in a patient at risk for thrombus formation, said device comprising a source of energy to be implanted in the patient adjacent to or within a vessel or chamber containing flowing blood whereby the source of energy, when activated, provides energy to the flowing blood within the vessel or chamber so that blood movement within the vessel or chamber is increased, thereby preventing thrombus formation or reducing the risk of thrombus formation. Additionally, the devices and methods of the present invention provide energy to the surface of the chamber or vessel, thereby preventing or reducing thrombus growth at the blood/surface interface.

The present invention also provides a method for improving blood flow within a vessel or chamber in a patient, said method comprising providing the patient with a source of energy adjacent to or within a vessel or chamber containing flowing blood and activating the source of energy to provide energy to the flowing blood within the vessel or chamber whereby blood movement within the vessel or chamber is increased, thereby improving blood flow within the vessel or chamber.

BRIEF DESCRIPTION OF THE FIGURES

FIG. 4 provides another embodiment of the present device (transducer 10 and implantable controller or ECM 12 connected via electrical lead wire assembly 14) in combination with an external input/output device or controller.

FIG. 5 provides several illustrations of possible ultrasonic pulse patterns that may be generated with the device of the present invention. Panel A: variation of frequency and amplitude; panel B: variation of pulse duration; panel C: period or interval between ultrasonic pulses.

DETAILED DESCRIPTION OF INVENTION

Figure 1:
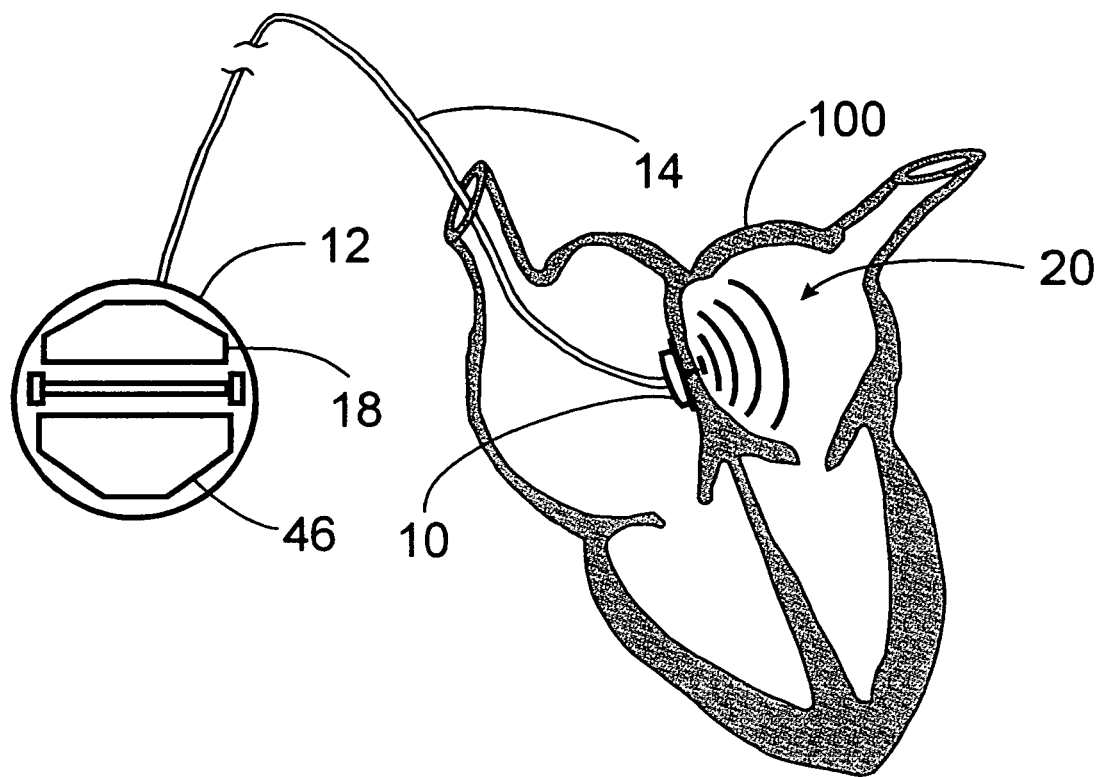
FIG. 1 illustrates one embodiment of the present device implanted in the heart to increase blood movement and/or flow within the left atrium 100. The device generally includes a high frequency ultrasonic transducer 10 and an implantable controller 12 (i.e., electronic control module or ECM) connected via electrical lead wires or electrical lead wire assembly 14.

The present invention provides methods and devices to prevent or significantly reduce the risk of thromboembolism. More specifically, the present invention provides a mechanical means for the prevention of thromboembolism or for the significant reduction of the risk of thromboembolism. Potential applications are for prevention of blood clot formation in the atria in patients with atrial fibrillation, prevention of blood clot formation in the blood vessels or heart chambers in patients who are at risk, and prevention of blood clot formation on or near artificial heart valves or other artificial cardiovascular devices. An external source of energy (mechanical, vibration, ultrasound, heat, microwave, magnetic, energy in the electromagnetic spectrum, and the like) is applied either within or from without a vessel or chamber in which blood flows. Although not wishing to be limited by theory, the external applied energy appears to decrease thrombus formation by decreasing stasis, modifying blood/surface interactions, and/or direct effects on the clotting cascade. For example, decreased stasis may be achieved by: (1) cavitation of blood in a chamber/vessel and/or at the interface between the chamber/vessel and the blood pool (i.e., ultrasound, laser); (2) mechanical stirring or vibration of the blood (i.e., mechanical devices); (3) thermal convection (i.e., microwave); (4) propagation of a shock wave (i.e., electrical shock); (5) induced blood flow (i.e., ultrasound mediated acoustic streaming, magnetic fields). Applied energy may also have direct effects on the clotting cascade and platelet function which will decrease thrombus formation.

This device may be coupled with other cardiac devices such as pacemakers or defibrillators. The device may function continually or intermittently. Intermittent operation may be based on a time basis (repeated cycles of on and off) or on observable or sensed conditions to activate the device. For example, the device may be coupled with monitoring devices to measure the heart rhythm and/or blood flow whereby the device is activated when atrial fibrillation or stasis in blood flow is detected or observed and then turned off once the conditions subsides. The device may be implantable or externally applied. The device may be coupled with the administration of drugs to enhance effect. The device may be combined with either lower doses of coumadin (i.e., doses previously not shown to be effective in reducing the risk of thromboembolism), standard doses of coumadin, or other agents (or combinations of agents) that have been shown by themselves to be ineffective, or less effective than desired, in preventing thrombus formation to provide an enhanced drug/device therapy. The device may be combined with removal of the left atrial appendage. The device may be incorporated as part of another mechanical or electronic device or implanted within other devices or prostheses (i.e., as part of an artificial valve or part of an artificial heart) or within the vicinity of these devices. The device may be gated to function during certain phases of the cardiac cycle (i.e., during ventricular diastole).

FIG. 1 generally illustrates one embodiment of the present device implanted in the heart to increase blood movement and/or flow within the left atrium 100. The device generally includes a transducer 10 and an implantable controller or electronic control module (ECM) 12 which are connected via electrical lead wire assembly 14. The electrical lead wire assembly 14 is generally composed of two distinct electrically conductive wires, intended to create electrical continuity with transducer 10. Each wire is electrically insulated with sufficient protection to safely conduct the required voltage, current, and frequency of the applied electrical energy. In addition, the electrical lead wire assembly can be further enhanced to ensure sufficient durability in an implantable environment. The controller or ECM 12 generally has a power source 46 (e.g., battery) and a control circuit 18 to operate and power the transducer 10. The transducer 10 provides directed energy 20 into the left atrium to prevent or reduce blood stasis and thereby prevent or significantly reduce the risk of thrombus formation. The transducer 10 should, of course, be sized to effectively fit within the heart chamber without interfering with the pumping activities; implantation techniques similar to those employed for pacemaker lead wire implantation can be used. The transducer could also be mounted on the exterior of the vessel or chamber (see, e.g., FIG. 3). Although not shown, the transducer 10, modified as appropriate, may be incorporated into an artificial heart device in order to reduce the risk of thrombus formation in such cases.

One preferred embodiment, which employs a transducer 10 using a piezoelectric transducer (PZT) or piezotransducer to generate ultrasound energy, is illustrated in FIGS. 2A (side view) and 2B (top view). This device is designed to periodically generate a directed burst of ultrasound energy directed into an area within a chamber or blood vessel where clotting is likely to occur and/or accumulate, thereby providing agitation and cavitation to surfaces and to fluids to prevent or reduce the risk of thrombus formation. The directed ultrasonic energy also enhances the motion of slow-moving circulating blood, further reducing the possibility of thrombus. In another preferred embodiment, the piezoelectric transducer (PZT) or piezotransducer is selected to generate high-frequency (ultrasound) energy in the range of about 250 kHz to about 2 MHz. Such a high frequency ultrasound generator would create an "acoustic streaming" effect, thereby causing rapid motion within the fluid subjected to the field. See, e.g., Zauhar et al., "Studies of acoustic streaming in biological fluids with an ultrasound Doppler technique," *Brit. J. Radiology*, 71, 297-302 (1998); Shi et al., "Quantitative investigation of acoustic streaming in blood," *J. Acoust. Soc. Am.*, 111(2), 1110-1121 (2002).

Figure 2:
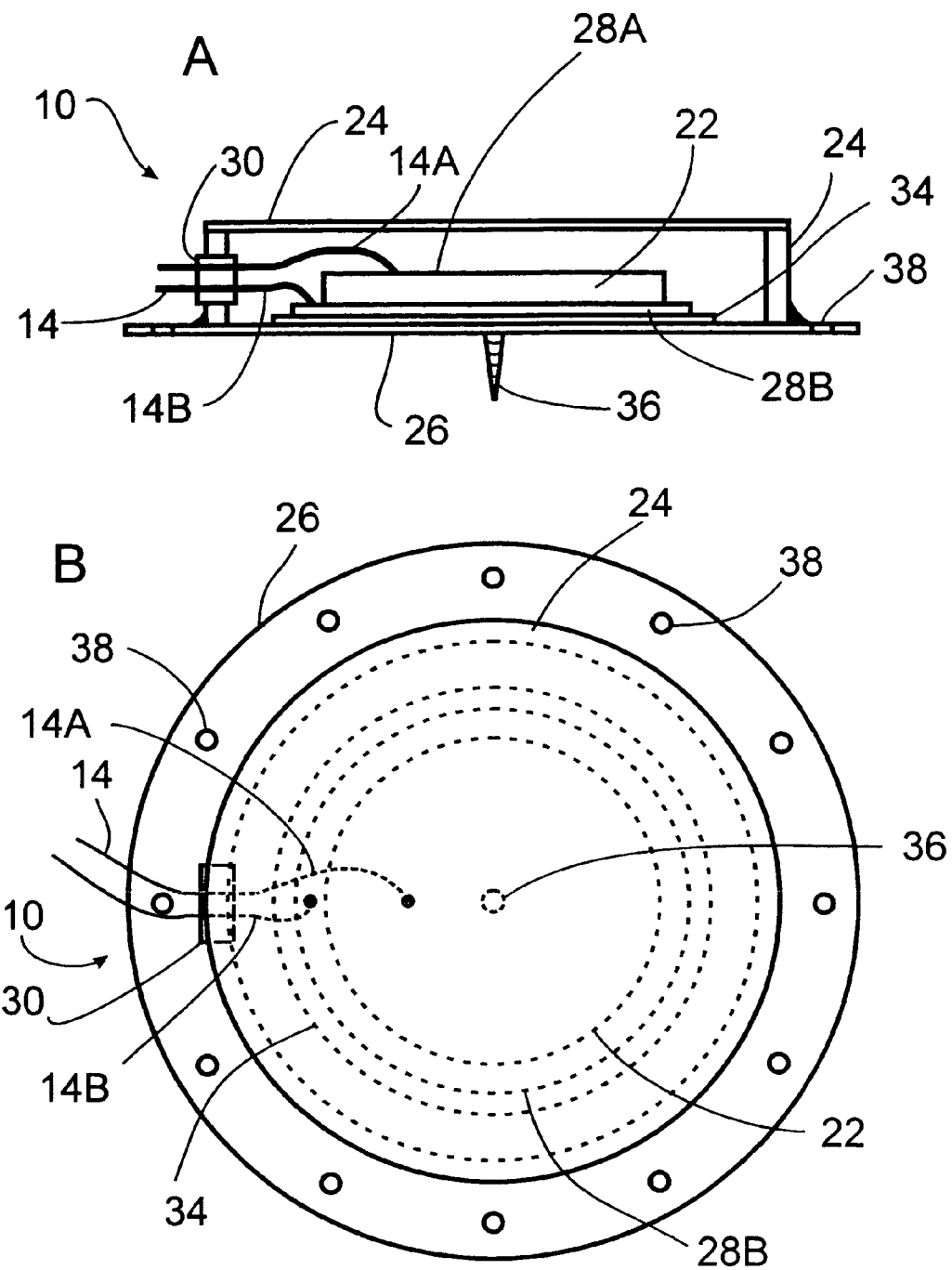
FIG. 2 provides a side (panel A) and top (panel B) of the transducer of the present device.

The device illustrated in FIG. 2 has a ceramic piezotransducer 22 positioned inside a housing 24, intended for implantation inside the patient. The PZT 22 is attached onto a housing base 26 which may be a vibrating plate or member to transmit lower frequency ultrasound to the vessel or tissue requiring the therapy or, more preferably, a member constructed of a material having properties suitable to provide low-acoustical impedance transmission of high-frequency ultrasonic energy or vibration to the vessel or tissue requiring the therapy.

Electrically conductive layers 28A and 28B are provided for each side of the PZT 22, enabling electrical contact from electrical lead wires 14A and 14B to the ceramic element. Thus, the internal lead wires 14A and 14B are employed to establish electrical contact to each side of the PZT 22. To isolate the device from the device housing (and patient), an insulating pad or layer 34 is placed between the electrically active device and the housing base 26. The housing 24 is attached to the housing base 26, thereby sealing and isolating the device interior from the patient. The housing base 26 should allow transmission of the energy from the device to the vessel or tissue being treated. A suitable housing base 26 could, for example, include a vibrating plate or member to transmit lower frequency ultrasound to the vessel or tissue requiring the therapy or, more preferably, a member constructed of a material having properties suitable to provide low-acoustical impedance transmission of high-frequency ultrasonic energy or vibration to the vessel or tissue requiring the therapy. Even more preferably, the housing base 26 is a member constructed of a material having properties suitable to provide low-acoustical impedance transmission of high-frequency ultrasonic energy or vibration to the vessel or tissue requiring the therapy and which can result in an acoustical streaming effect. An electrical pass-through 30 is designed into the housing 24, in order to connect the exterior lead wire assembly 14 to the internal electrical lead wires 14A and 14B.

The internal/external lead wires and pass-through connector 30 can be screwed, crimped, soldered, or welded and subsequently over-molded with an insulating polymer in order to establish electrical and mechanical integrity. Biologically compatible materials and processes known to those skilled in the implantable medical device arts can be employed in the design and manufacture of the housing and electrical lead wires (e.g., titanium housings, silicone or polyurethane-encapsulated electrical lead wires, and the like). The housing can employ a mounting spike and/or mounting screw 36 or mounting holes 38 to secure the device, using known techniques, onto the exterior or interior surface of an organ, vessel, or tissue requiring the ultrasound therapy.

Figure 3:
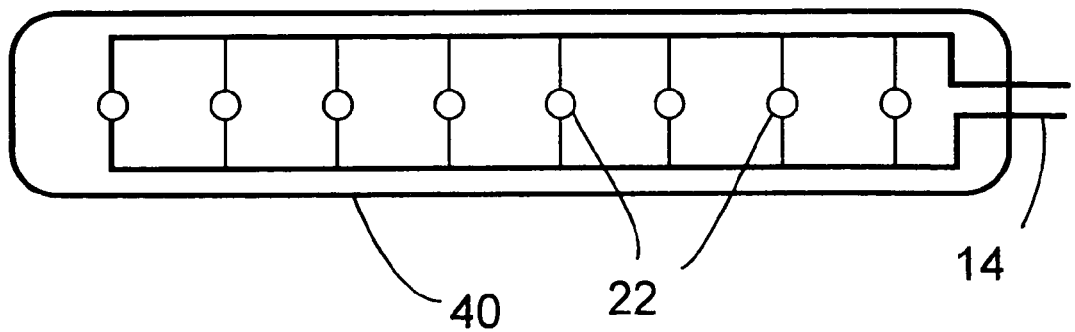
FIG. 3 illustrates another embodiment of the present device for preventing thrombus at or near an artificial heart valve. Panels A (flexible sheet) and B (the flexible sheet configured into a "collar") illustrate the transducer itself; panel C illustrates the transducer relative to an implanted artificial heart valve.
Figure 3:
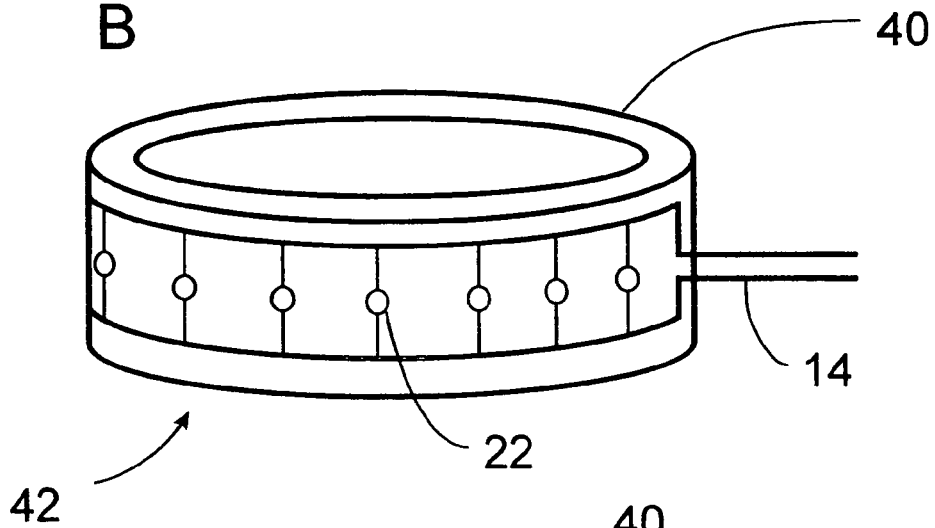
Figure 3:
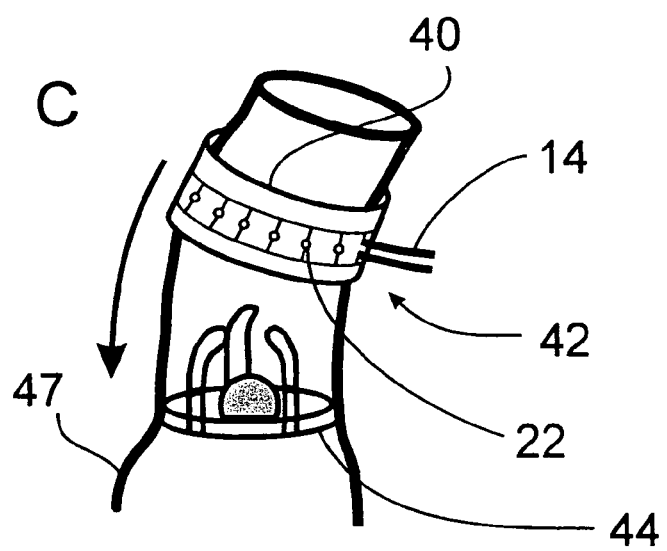

Employing the basic design described above, multiple PZT devices can be configured to surround, encircle, or enhance a unique location requiring thrombus therapy as shown in FIG. 3. For example, an array of PZT's can be arranged on a flexible sheet 40; such a flexible sheet 40 could be attached to, or adjacent to, the vessel or tissue to be treated, or could be subsequently configured into a "collar" 42 (as illustrated in FIGS. 3B and 3C), in order to prevent the build-up of a life-threatening thrombus in the proximity of the vessel or tissue to be treated such as, for example, an implanted heart valve 44 as illustrated in FIG. 3C. The arrow in FIG. 3C indicates the collar 42 is to be slipped down to be adjacent to, or effectively "surround," the implanted heart valve 44 within the vessel or chamber 47.

The lead wire assembly 14 is used to attach the transducer 10 to a separate electronic control module (ECM) 12, thereby allowing for remote positioning of the ECM 12 in a suitable location on or within the human body. The lead wire assembly 14 can be of varying length, in order to provide the clinician with flexibility for locating and implanting the ECM 12 at a desired location. Similar means of attaching the lead wire assembly 14 to the PZT electrical pass-through 30 can be employed to attach the lead wire to the ECM 12.

As illustrated in FIG. 4, the electronic control module 12 consists of a battery 46, hybrid microcircuit 48, radio-frequency transmitter/receiver circuit 50, and antenna 52. The ECM 12 employs a sealed exterior housing 54 to isolate the device from the patient, as well as to protect the battery 46 and associated control circuitry from the environment within the human body. An electrical pass-through 56, similar to the PZT housing pass-through 30, is designed into the exterior of the ECM housing 54. The lead wire may be attached to the ECM 12 by the health care provider using standard techniques.

Preferably the battery 46 is a long-life battery similar to those employed by pacemakers and other implanted medical devices. A separate voltage regulator 58 can be employed in order to provide the circuit with stable direct current (DC) voltage to power the device. The battery source could consist of a hydrogen-oxygen fuel cell, rechargeable battery, or any other suitable means of providing an electrical source of power. Preferably, the ECM 12 is located within the patient at a location which facilitates, when necessary, battery and/or ECM replacement.

The hybrid microcircuit 48 contains a function generator 60, capable of generating a high-frequency, alternating current (AC) signal. The device can, for example, employ sinusoidal signal (or square wave, saw tooth, or other time variant signal) generated by an oscillator, microprocessor, or integrated electronic circuit known to those skilled in the electrical engineering and hybrid microelectronic arts. Typically such a signal will be in the range of about 25 kHz to about 2 MHz. Preferably a high frequency signal (i.e., about 250 kHz to about 1 MHz) will be used; even more preferably, a high frequency signal which generates acoustical streaming will be employed. The amplifier section 62 on board the control circuit would be driven off of the generated signal, providing the necessary voltage and current levels required to power the PZT 22. The amplifier circuit can consist of an arrangement of transistors, transformers, and other electrical components designed to power the PZT 22 with the voltage and current required for ultrasound generation. A microprocessor 64 on board the hybrid microcircuit would provide the means to control the frequency, amplitude, and duration of the electrical signal powering the PZT 22. In addition, the microprocessor 64 can be employed to store/adjust the desired operating parameters, monitor the battery strength, provide status of the various circuit elements, or store data for later retrieval. For multiple PZT configurations (e.g., as shown in FIG. 3), the microprocessor 64 could also provide a unique timing sequence of device activation. For example, the PZT array could be activated in order to generate various interference patterns for the converging ultrasonic wave fronts.

The regulator, signal generator, amplifier, and microprocessor functions can be integrated to conserve space and electrical power, as well as improving device reliability and durability. A peripheral timer/clock element 66 can also be employed to power down the circuit when not in use in order to conserve battery power. The device can employ redundant circuitry, default operating parameters, and other safety features to ensure safe operation in the event of device failure or malfunction.

The ECM 12 can transmit useful information (e.g., commands, status information, health information, and the like) to the health care provider by means of the radio-frequency (RF) circuit 50 via the device antenna 52. For example, the microprocessor 64 can monitor the battery strength, and provide a "low battery" warning for transmission to the health care provider. In addition, the health care provider could routinely adjust the pulse duration, amplitude, power output, or frequency of the applied energy (see, e.g., FIG. 5) to the PZT 22.

A microprocessor-based programmer 70 can be employed to enable the health care provider to program the device, to adjust the device performance after implantation, and to query the device performance and status. The programmer 70 could consist of a microprocessor-based programming device (i.e., hand-held device, personal digital assistant, laptop or desktop computer, or the like) equipped with appropriate programming and control software and having a radio-frequency (RF) link 72, designed to communicate with the implanted unit or ECM 12, via wireless communication means 74. Using a graphic user interface 76 of the computing device and appropriate input device 77 (e.g., mouse, keyboard, or other input device), the health care provider could use the appropriate programming or control software to select the appropriate subroutines for initial start up, device programming, adjustment of the implanted device, device query as to its current status, and the like. The health care provider could also use the programmer 70 to assess health care information that may be stored in the microprocessor 64 (e.g., pulse rate over time, number and length of atrial fibrillation episodes, irregular heart rhythms, and the like). Additionally, using telephone or similar services (ground or wireless based), information can be relayed directly to the health care provider on a periodic basis or when alarm conditions so warrant.

Generally, the present device operates in the following fashion. Prior to or after implanting the device, the health care provider would power up the device and/or program the unit with initial operating parameters suitable for the patient's condition. Device start-up and programming would be conducted by means of the programmer 70, which would upload the operating parameters into the device's microprocessor 64, via the radio-frequency transmitter/receiver circuit 50 of the ECM 12. The PZT housing 24 containing the piezotransducer 22 would then be attached to the patient's organ or body tissue, suitably located for optimal transmission of the ultrasonic energy to the area requiring the thrombus-prevention therapy. The physician would employ the mounting spike or screw 36 or mounting holes 38 to securely attach the device to the patient. If required, the lead wire assembly 14 would be threaded within the patient in order to locate and secure the electronic control module 12 in a body cavity or other suitable locale.

The microprocessor and timing circuits in the electronic control module 12 would periodically turn on the function generator 60, generating the high-frequency signal needed to drive the amplifier circuit 62. The amplifier signal would power up the piezotransducer 22 via the external lead wire assembly 14. The piezotransducer 22 would then vibrate at the selected frequency and the selected duration, thereby generating an acoustic wave front. The ultrasound energy would then be transmitted to the area of interest to provide effective agitation, stirring, or cavitation. The high-frequency energy imparted by the device would prevent or significantly reduce the build-up of life-threatening thrombus.

Figure 6:
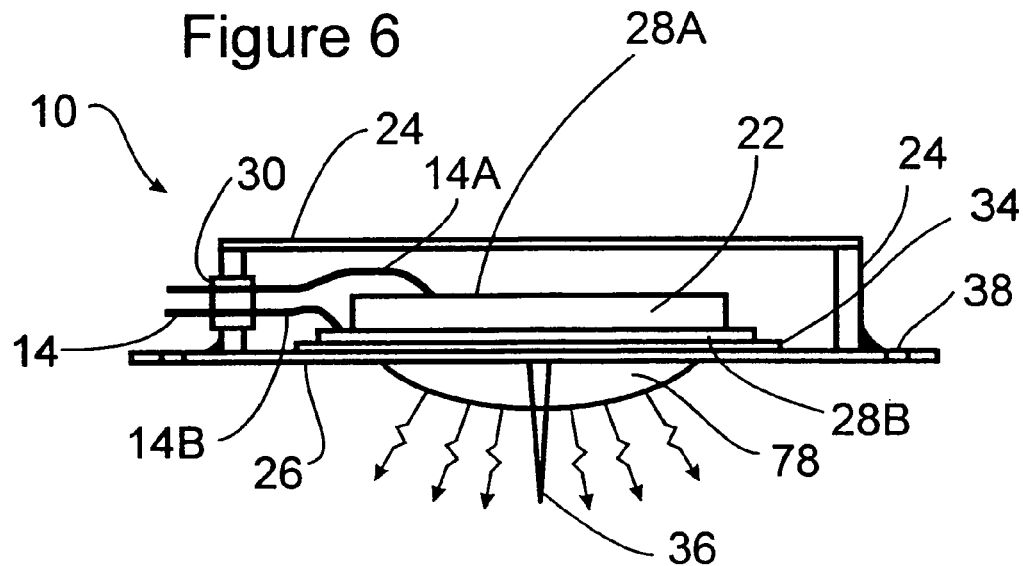
FIG. 6 provides another embodiment of the transducer in which a diverging acoustic lens 78 is used to generate a wider field of ultrasound.
Figure 7:
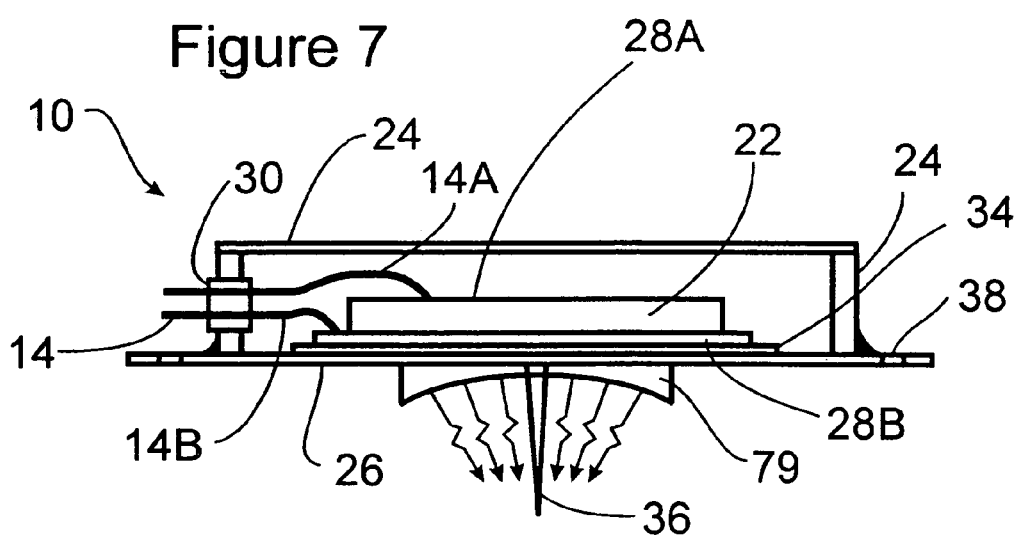
FIG. 7 provides another embodiment of the transducer in which a converging acoustic lens 79 is used to generate a more focused area of ultrasound.

Similar to light frequencies, the ultrasound wave front can be focused or de-focused in order to provide, respectively, (1) more focused or concentrated thrombus reduction therapy (see FIG. 7) or (2) greater areas of thrombus reduction therapy (see FIG. 6). In order to increase the area undergoing thrombus-reduction therapy, a diverging acoustic lens 78 (see FIG. 6) can be attached to the device housing base 26 of transducer 10. In order to provide a more focused area for thrombus-reduction therapy, a convergent lens 79 (see FIG. 7) can be attached to the device housing base 26 of transducer 10.

The microprocessor 64 could be used to adjust and/or control the frequency, amplitude, and power output of vibration (see, e.g., FIG. 5A) as well as the duration of the ultrasonic pulse (see, e.g., FIG. 5B), and/or the period or interval between ultrasonic applications (see, e.g., FIG. 5C). The device could be configured or programmed to provide different stimulation profiles throughout the day and/or different stimulation profiles depending on the current physical condition of the heart and/or blood flow in the chamber or vessel of interest. The stimulation profile may incorporate a frequency and amplitude sweep to more efficiently deal with the varying geometries of the blood/surface interfaces. Of course, other stimulation patterns, or combinations of patterns, could also be used.

This device can be combined with or incorporated into other cardiovascular devices, such as heart valves, grafts, or any artificial implant susceptible to thrombus formation. The ultrasonic device can also be combined with or incorporated into other therapeutic devices, such as pacemakers, defibrillators, nerve stimulators, and local drug delivery devices that are used to achieve optimal control of the underlying cardiac condition.

The device also can be used in combination with medications that are designed to prevent or reduce thrombus formation. The use of this device in combination with such medications should allow reduced dosage levels, thereby preventing or reducing the risk of side effects associated with the drug.

The ultrasonic device also can be configured where the generated ultrasonic pulse is synchronized to the natural cardiac rhythm of the heart. The device would trigger the ultrasonic pulse during a period of the cardiac rhythm when the energy pulse can be most efficiently directed into the area requiring therapy. In order to synchronize the ultrasonic pulse with the cardiac rhythm, a separate circuit could be incorporated into the electronic control module to monitor the patient's cardiac rhythm. The sensing circuit would be similar to those employed in implantable devices such as pacemakers. The sensing circuit may also be used to monitor the heart rhythm for detection of atrial fibrillation episodes in patients with paroxysmal atrial fibrillation (sudden onset and cessation of atrial fibrillation of variable duration). Device therapy may be timed to the onset and offset of atrial fibrillation episodes. For example, the device would begin to operate at the onset of an episode of atrial fibrillation. The device would continue to operate throughout the episode of atrial fibrillation. When sinus rhythm returns, the device would operate for a programmable period of time and then cease operation until another episode of atrial fibrillation is detected. This could provide assurance to the physician that life threatening thrombus formation is prevented or at least significantly reduced in patients with paroxysmal atrial fibrillation.

Example 1

In vitro testing using a 1 MHz ultrasound transducer was performed using two cube-shaped test fixtures with volumes of 125 and 275 cc (approximately simulating the range of clinically observed left atrial volumes (see, e.g., Weyman, "Left ventricular inflow tract II: The left atrium, pulmonary veins, and coronary sinus," In: Bussy R (ed.), *Principles and Practice of Echocardiography*, Philadelphia: Lea & Febiger, p. 471-497, (1994)) and outfitted with an internal plastic liner. The transducer was attached to the outside of the plastic liner through a hole that was machined through the side panel of the test fixture. To evaluate the effect of ultrasound on flow and acoustic streaming within the chamber, a drop of food coloring was placed in the chamber under control conditions (absence of applied ultrasound) and with applied ultrasound at acoustic power outputs ranging from 50 to 500 mW/cm$^2$. A digital video image obtained from above the fixture was used evaluate flow within the test fixtures as a function of time. In the absence of applied ultrasound (i.e., the control), the dye diffused slowly through the chamber; even at 60 seconds, the dye remained in the lower half of the chamber in the control test. When ultrasound was applied at 250 mW/cm$^2$, there was more rapid diffusion of the dye within the chamber due to the flow created by the applied ultrasound; within about 5 seconds, dye reached a side panel and within about 15 seconds was distributed throughout the chamber. When ultrasound was applied at 500 mW/cm$^2$, dye reached a side panel within about 1 second and was completely dispersed throughout the chamber by about 5 seconds. The more rapid distribution of dye within the chamber is due to acoustic streaming (which was also visible to the naked eye). In the large test chamber, evidence of acoustic streaming resulting in enhanced diffusion of the dye was noted at a threshold value of about 150 mW/cm$^2$ with increasingly rapid diffusion of dye as the power was increased. In the small test chamber, evidence of acoustic streaming was noted at a threshold value of about 100 mW/cm$^2$ with increasingly rapid diffusion of dye as the power was increased. Thus, there is a strength-effect relationship that is also dependent on the size of the chamber in which the ultrasound is applied. These findings demonstrate that an ultrasound based implantable device can be used to achieve enhanced flow.

Although the device has been described in detail using ultrasonic energy, similar devices using other directed energy means can be used using appropriate modification known in the art. Thus, for examples, devices employing ultrasonic energy, mechanical energy, vibrational energy, heat energy, microwave energy, magnetic energy, energy in the electromagnetic spectrum, and the like can also be used. Generally, however, ultrasonic energy is preferably used.

I claim:

1. An implantable device for a patient at risk for thrombus formation in the patient's heart, said device comprising a source of energy to be implanted in the patient near, adjacent to, or within a chamber of the heart containing flowing blood whereby the source of energy, when activated, provides energy directly to the flowing blood within the chamber so that blood movement within the chamber is increased by an amount effective to reduce the risk of thrombus formation in the patient's heart, wherein the energy provided to the flowing blood is high frequency ultrasound energy with a frequency of about 250 kHz to about 1 MHz and a power output sufficient to provide acoustical streaming in the flowing blood.

2. The implantable device as defined in claim 1, wherein the power output is about 50 to about 500 mW/cm$^2$.

3. The implantable device as defined in claim 2, wherein the ultrasonic energy is provided by a piezoelectric transducer.

4. The implantable device as defined in claim 3, wherein the source of energy comprises a transducer located near, adjacent to, or within the chamber to provide the energy and a remote controller in electrical communication to the transducer and located in a remote location on or within the patient, wherein the remote controller contains a power source and microelectronic circuits to operate and control the transducer.

5. The implantable device as defined in claim 1, wherein the source of energy comprises a transducer located near, adjacent to, or within the chamber to provide the energy and a remote controller in electrical communication to the transducer and located in a remote location on or within the patient, wherein the remote controller contains a power source and microelectronic circuits to operate and control the transducer.

6. The implantable device as defined in claim 5, wherein the remote controller further contains a radio-frequency circuit, a device antenna, and an electronic communication device external to the patient which is in communication with the remote controller via the radio-frequency circuit and the device antenna and can be used by a health care provider to program and control the source of energy.

7. The implantable device as defined in claim 4, wherein the remote controller further contains a radio-frequency circuit, a device antenna, and an electronic communication device external to the patient which is in communication with the remote controller via the radio-frequency circuit and the device antenna and can be used by a health care provider to program and control the source of energy.

* * * * *